(12) United States Patent
Sobczak

(10) Patent No.: US 6,514,540 B1
(45) Date of Patent: Feb. 4, 2003

(54) THERAPEUTIC COMPOSITION INCLUDING PLANTAIN AND ALOE VERA FOR TREATMENT OF ARTHRITIS AND OTHER AFFLICTIONS

(76) Inventor: Nancy Laning Sobczak, c/o Nancy Laning Sobczak Consulting, 2509 N. Humboldt, Milwaukee, WI (US) 53212

( * ) Notice: Subject to any disclaimer, the term of this patent is extended or adjusted under 35 U.S.C. 154(b) by 0 days.

(21) Appl. No.: 09/947,695

(22) Filed: Sep. 6, 2001

Related U.S. Application Data

(62) Division of application No. 09/358,223, filed on Jul. 21, 1999, now Pat. No. 6,309,675.

(51) Int. Cl.⁷ ............................................. A61K 35/78
(52) U.S. Cl. ..................... 424/738; 424/744; 424/725; 424/774; 514/825
(58) Field of Search ................. 424/738, 744, 424/725, 774; 514/825

(56) References Cited

U.S. PATENT DOCUMENTS

| | | | | |
|---|---|---|---|---|
| 5,578,312 A | * | 11/1996 | Parrinello | 424/401 |
| 5,738,850 A | * | 4/1998 | Hendricks et al. | 424/195.1 |
| 5,843,467 A | * | 12/1998 | Ambroziewigz | 424/401 |
| 5,882,666 A | * | 3/1999 | Averill et al. | 424/401 |

FOREIGN PATENT DOCUMENTS

| | | | |
|---|---|---|---|
| EP | 0636373 | * | 2/1995 |
| HU | 50623 | * | 3/1990 |
| HU | 33033 | * | 10/1994 |
| RU | 2121341 | * | 11/1998 |

OTHER PUBLICATIONS

Tyler, V. Herbs of Choice. Haworth Press, Inc., Birmingham, NY, pp. 92–93 and 155–157.*

Pierce, A. Am. Pharm. Assoc. —Practical Guide to Natural Medicines, pp. 31–35.*

* cited by examiner

*Primary Examiner*—Christopher R. Tate

(57) ABSTRACT

A therapeutic composition for treating arthritis and other afflictions includes plantain and *aloe vera* constituents, which are approximately 0.01% to 0.1% and 0.1% to 1.0% by weight of the therapeutic composition, respectively. Other constituents, such as herbal tinctures, added for various purposes, may be approximately 5% to 10% by weight of the therapeutic composition. A joint compatible solution for injection directly into a human joint makes up approximately 99 to 99.9% by weight of the plantain constituent, and approximately 90 to 99.9% by weight of the *aloe vera* constituent, with the remaining approximately 0.1 to 1.0% by weight of the plantain constituent being extract from a plantain plant and the remaining approximately 0.1 to 10.0% by weight of the *aloe vera* constituent being extract from an *aloe vera* plant. The plantain extract acts as a medication, while the *aloe vera* extract acts as a vehicle to carry the plantain extract.

17 Claims, No Drawings

THERAPEUTIC COMPOSITION INCLUDING PLANTAIN AND ALOE VERA FOR TREATMENT OF ARTHRITIS AND OTHER AFFLICTIONS

This is a Divisional application of Ser. No. 09/358,223 filed Jul. 21, 1999, which issued as U.S. Pat. No. 6,309,675, the entire contents of which are incorporated by reference.

FIELD OF THE INVENTION

The present invention generally relates to compositions of matter and more particularly, to a therapeutic composition including plantain and *aloe vera* as its main ingredients in a particular percentage by weight arrangement with respect to each other in order for the therapeutic composition to be useful in the treatment and relief of the symptoms of arthritis and other afflictions.

BACKGROUND OF THE INVENTION

Plants and herbs have long been used for medicinal purposes. Indeed, native Americans have long known of the healing powers of certain herbs as remedies for various illnesses. However, much research still needs to be done in the area of herbal remedies and it is believed that present day healers have only begun to scratch the surface of the limitless possible cures offered by plants and herb.

One recent inroad into herbal cures came with the discovery that *aloe vera* may be used as a biological vehicle for the delivery of drugs. U.S. Pat. No. 5,708,038 (the '038 patent) discloses an embodiment wherein *aloe vera* is used as a biological vehicle to deliver the estrogen, β-estradiol and the androgen, testosterone propionate. The '038 patent also discloses a method of treating symptoms and diseases mediated by hormonal deficiencies or amenable to treatment by hormones using *aloe vera* as the biological vehicle for allowing penetration of drugs via a topical method.

Another example of using plants and herbs for medicinal purposes is disclosed in U.S. Pat. No. 5,192,542 which teaches that plantain may be used in a product for treating tissue to form closures of wounds, incisions, and other openings, particularly during the embalming process.

Other well known examples of using plants and herbs for medicinal purposes include: aspirin, which comes from the bark of a white willow tree; and digitalis, which comes from a flower commonly known as fox glove.

The present invention provides a therapeutic composition which combines the healing powers of plantain and *aloe vera* (also known simply as aloe) for use in the treatment of arthritis and other afflictions, such as hematomas, skin rashes and infections.

Arthritis is a disease characterized by an inflammation of the joints, such as the knees, wrists, elbows, fingers, toes, hips, shoulders, and neck and back (i.e., joints between the bones of the spine). The inflamation characteristic of arthritis is often accompanied by other symptoms such as mild to severe pain, swelling, weakness in associated areas, and deformity. Arthritic symptoms may come on gradually or appear suddenly. Some people feel sharp burning or grinding pain, while others compare the pain to a dull toothache. Movement of the joints is usually associated with pain, although sometimes there is only stiffness. In general, there is usually a pronounced weakness in the muscular strength in the affected area.

The onset of the disease of arthritis can be associated with physical or emotional stress, age, poor nutrition, age, and possibly bacterial infections or other maladies or dysfunctions of unknown origin.

Furthermore, other diseases of the highly vascular area of the head, including the mouth, throat, particularly, the teeth and tonsils, and the nose and sinuses, may play a role in the onset or intensification of the symptoms of arthritis.

Arthritis can manifest itself in many different forms. For instance, one common form of arthritis is osteoarthritis which is a degenerative joint disease related to the wear and tear or aging of the joint and involves deterioration of the smooth cartilage.

Other types of arthritis include rheumatoid and juvenile rheumatoid arthritis which can attack the synovial membranes surrounding the lubricating fluid in the joints. Often, the bone tissue and the cartilage and tissues in and around the joints are destroyed. The body replaces this damaged tissue with scar tissue which causes the spaces between the joints to become narrow in order to develop folds and to fuse together. The entire body is affected instead of just one joint as with other forms of arthritis. The disease creates stiffness, swelling, fatigue, anemia, weight loss, fever, and often crippling pain.

Another type of arthritis is ankylosing spondylitis (AS) which affects certain joints of the spine that become inflamed, stiffen, become rigid, and then, fuse together. If confined to the lower back, AS will cause virtually no limitation of movement. However, in some cases, the entire spine may become rigid and bent. If the joints between the ribs and spine are affected, severe breathing problems may result due to the limited expansion of the chest wall.

Another type of arthritis, systemic lupus erythematosus (SLE), involves a malfunction of the body's immune system. For reasons unknown, the body produces antibodies that act against itself. Although it mimics rheumatoid arthritis and results in painful and inflamed joints, SLE is not a crippling disease.

A therapeutic composition useful in the treatment of arthritis and other afflictions would be an important advance in managing the subject's symptoms.

It is an object of the present invention to provide a therapeutic composition of matter which combines the healing powers of plantain and *aloe vera* to treat arthritis and other afflictions.

SUMMARY OF THE INVENTION

The present invention relates to a therapeutic composition including: a plantain constituent which is in a range of approximately 57% to 61% by weight of the therapeutic composition; and an *aloe vera* constituent which is in a range of approximately 39% to 43% by weight of the therapeutic composition (in the case of topical applications).

The therapeutic composition may also include other constituents, such as any one or more of a group consisting of alfalfa leaf, dandelion root, licorice root, devils' claw, feverfew, chamomile, willow bark, either mullein leaf or tumeric, and either yucca or burdock. These other constituents are herbs that can be added to the main ingredients of the plantain and *aloe vera* for specific purposes, such as to act as an anti-inflammatory, a diuretic, a healing agent, or to act to remove poisons from the system, to reduce localized heat production, such as "hot spots," or fever, etc. If the therapeutic composition contains other constituents, then the percentages of the plantain, *aloe vera* and other constituents are as follows: the plantain constituent is in a range of approximately 51% to 58% by weight of the therapeutic composition; the *aloe vera* constituent is in a range of approximately 37% to 39% by weight of the therapeutic composition; and the other constituents are in the range of approximately 5% to 10% by weight of the therapeutic composition (in the case of topical applications).

Regardless of whether the therapeutic composition includes other constituents, the plantain constituent may include a glycerin-based cream or lotion which is in a range of 99 to 99.9% by weight of the plantain constituent and a plantain extract which is in a range of 0.1 to 1.0% by weight of the plantain constituent. The *aloe vera* constituent may include a glycerin-based cream or lotion, which is in a range of 90 to 99.9% by weight of the *aloe vera* constituent, and an *aloe vera* extract, which is in a range of 0.1 to 10.0% by weight of the *aloe vera* constituent. Preferably, the *aloe vera* extract is derived from an *Aloe barbadensis* plant.

The plantain extract acts as a medication, while the *aloe vera* extract acts as a vehicle to carry the plantain extract through the skin barrier of a person on whom the therapeutic composition is topically applied in order to treat and relieve the symptoms of arthritis and/or other such treatable afflictions.

In another embodiment of the present invention, the plantain extract and *aloe vera* extract are contained in a joint compatible solution for injection directly into a joint (or a muscle near or surrounding the joint) of an applicant. The joint compatible solution may be a ringers-type solution or any other suitable isotonic substrate. In the case of injection directly into the joint, the plantain constituent would be in the range of approximately 0.01 to 0.1% by weight of the therapeutic composition and the *aloe vera* constituent would be in the range of approximately 0.01 to 1% by weight of the therapeutic composition (i.e., more diluted, since the therapeutic composition does not have to go through the skin and muscle layers as it does with a topical application).

In another embodiment of the present invention the plantain and *aloe vera* extracts are combined with any oral hygiene agent. The combination of plantain, *aloe vera*, and oral hygiene agent is then included in a toothpaste base for good oral hygiene and aiding in the cleansing of the mouth.

Finally, in another embodiment of the present invention, the plantain and *aloe vera* extracts are combined with a saline solution of approximately 0.05% concentration for use as a nasal spray.

DETAILED DESCRIPTION OF THE INVENTION

The present invention involves a composition of matter having plantain and *aloe vera* as its main ingredients. The composition of matter containing plantain and *aloe vera* is a therapeutic composition for use in the treatment and relief of the symptoms of arthritis, in particular, and other afflictions, such as, but not limited to, hematomas and skin rashes and infections. The plantain extract acts as a medication, while the *aloe vera* extract acts as a vehicle to carry the plantain extract through a skin barrier of an applicant on which the therapeutic composition is topically applied in order to treat and relieve symptoms of arthritis and other diseases.

The therapeutic composition of the present invention may include only a plantain constituent and an *aloe vera* constituent, in which case the plantain constituent is in a range of approximately 57% to 61% by weight of the therapeutic composition and the *aloe vera* constituent is in a range of approximately 39% to 43% by weight of the therapeutic composition.

The therapeutic composition may also include other constituents, such as any one of a single constituent and a plurality of constituents from a group consisting of alfalfa leaf, dandelion root, licorice root, devils' claw, feverfew, chamomile, willow bark, mullein leaf, tumeric, yucca and burdock. These other constituents are herbs that can be added to the main ingredients of the plantain and *aloe vera* to provide additional therapeutic efficacy or value.

More specifically, the plantain, *aloe vera*, and other possible ingredients (i.e., herbal tinctures or vitamins) of the therapeutic composition of the present invention are summarized in TABLE I below with respect to a description thereof, the active ingredients therein, and the benefits thereof.

TABLE I

| | DESCRIPTION | ACTIVE INGREDIENTS | BENEFIT |
| --- | --- | --- | --- |
| Aloe Vera | Aloe vera is a perennial plant found wild in East and South Africa. It is also cultivated in the West Indies and other tropical areas. It has also been reported in the Zapata area of Texas. It is also called barbados aloe vera and curacao aloe vera. The strong, fibrous root produces a rosette of fleshy basal leaves as in the agave, but considerably smaller. The narrow-lanceolate leaves are 1 to 2 feet long and whitish-green on both sides, and they bear spiny teeth on the margins. | Carrisyn, salicylates, enzyme that inhibits bradykinin (pain transmitter), magnesium lactate, compounds that exhibit bacteriostatic and antifungal activity. | It is used to conduct the active ingredient of the herbs through the skin barrier. |
| Plantain | Plantago major (Plantain) can be described as an annual, biennial, or perennial herb with upwards of two-hundred-seventy species. It produces rosettes of glabrous or pubescent, ovate to elliptical leaves. It can be described by the names, as follow: plantain rugelii, English plantain (lanceolata), sand plantain (patagonica), rattlesnake plantain (goodyera pubescen), water plantain (alisma plantago aquatica), common plantain, broad-leaved plantain, greater plantain, round-leaved plantain, way bread, white man's foot, lance-leaf plantain, buckhorn, chimney-sweeps, headsman, ribgrass, ribwort, ripplegrass, snake plantain, and solder's herb. Plantain is closely associated with the activity of man. It is widely distributed throughout the world, even at high elevations (2800 m in Valais, Switzerland). It has a truly remarkable wide range of | Vitamins C, D, E, and K | It is used as a healing agent. |

TABLE I-continued

| | DESCRIPTION | ACTIVE INGREDIENTS | BENEFIT |
|---|---|---|---|
| | distribution as it occurs from pole to pole, although apparently absent from the lowland tropics. It is clearly cosmopolitan. Plantain occurs in a very wide range of soil types such as loarn, clay, and sand. It is a common species of cultivated soil, waste ground, and roadsides. The growing season in northern areas of the USA occurs from mid-April to late October. Flowering can be continuous over mid-June to October, with a peak in July. Plantain is a long day plant and flowering fails unless the photoperiod is greater than 13 hours. The fruits mature 2 to 3 weeks after anthesis. Seeds are always viable and germinate intermittently throughout the growing season. Plantain is easily spread, since it is wind pollinated and capable of full self-fertilization. | | |
| Alfalfa Leaf | Alfalfa is a perennial plant found on the borders of fields, in low valleys, and widely cultivated. The erect, smooth stem grows from an elongated taproot to a height of 12 to 18 inches and bears pinnately trifoliate leaves with oblong-obviate or linear-oblong leaflets. The blue or purplish flowers grow in racemes from June to August, producing finally the characteristic spirally coiled seedpods. | Saponins, L-canaverine (non-protein amino acid). | It is used as a diuretic and a healing agent. |
| Dandelion Root | The dandelion is a perennial plant found almost everywhere. The oblong or spatula, irregularly dentate or pinnatifid leaves, grow in a rosette from the milky taproot, which also sends up one or more naked flower stems, each terminating in a single yellow flower. The familiar puffball that succeeds the flower is a globular luster of achenes, each of which is fitted with a parachute like tuft. | Vitamins A and C | It acts to remove poisons from the body. |
| Licorice Root | Licorice is a perennial plant found wild in southern and central Europe and parts of Asia, and cultivated elsewhere. The woody rootstock is wrinkled and brown on the outside, yellow on the inside, and tastes sweet. The stem, which is round on the lower part and angular higher up, bears alternate, odd-pinnate leaves with 3 to 7 pairs of ovate, dark green leaflets. Axially racemes of yellowish or purplish flowers appear from June to August, depending on location. | Glycosides, flavonoids, asparagine, isoflavonoids, chalcones and coumarins. Glycyrrhetrinic acid (anti-inflammatory), glycyrrhetrinic (anti-viral). Others act as anti-depressants and inhibit enzymes that cause tooth decay. | It acts as a diuretic and a healing agent. Since it is high in Iron, it also enhances oxygenation of the body and acts as a magnetic ion in the system. |
| Devil's Claw | The plant grows in the rugged Kalahari Dessert and is named for the plant's elaborate thorny structure. | Harpogoside and Beta-sitosterol (anti-inflammatory properties). | Historically, it has been used to treat arthritis. |
| Feverfew | Feverweed is a sticky and hairy, annual or perennial plant that grows in dry woods and thickets from Maine to Florida and west to Ontario, Minnesota, and Missouri. The numerous stems are 1 to 4 feet high and bear opposite, fernlike leaves, 1 to 3 inches long, which are pintail lobed and deeply serrated. The large, yellow, bell-shaped flowers grow in loose terminal racemes in August and September. | Sesquiterpene lactone, parthenolide (inhibits production and secretion of prostaglandis-substances released by blood platelets and white blood cells which contribute to inflammation). | It is particularly effective in producing fever in the body. |
| Chamomile | There are two primary types of chamomile: Roman chamomile and German chamomile. It is a perennial plant found in Hungary, the Czech Republic, Slovakia, Germany, Argentina, and Egypt. Roman (or English) chamomile is aldo available, but to a lesser extent in the American market. It is a member of the daisy family and grows from four to twenty-four inches tall in disturbed ground, commonly farmyards. If has firmly cut leaves with flower petals in white rays and discs of yellow and an ill-scented aroma. | Essential oils, volatile oil bisabolol, flavonoid apigenin (anti-anxiety and useful in supporting alpha bisabolol - an anti-inflammatory and anti-spasmodic. | It is used to decrease inflammation. |
| Yucca | Yucca root comes from the flowering yucca plant which is a member of the lily family that can grow to heights of 40 feet or more. | Steroid-like saponins that elevate the body's production of cortisone. | It acts an anti-inflammatory. |
| Burdock Root | Burdock is a biennial plant found in northern U.S. and in Europe, along fences, walls, and roadsides, in waste places, and around populated areas. The root is long, fleshy, gray-brown outside and whitish inside. In its second year, the plant grows a furrowed, reddish, pithy stem with wooly branches. During the first year, burdock has only basal leaves. Both basal and stem leaves are oblong-cordate to cordate, green and hairy on top and downy gray beneath. The purple flowers appear in loose corymbose clusters from July to September. | High in minerals (good source of iron), good source of essential oils, compounds that exhibit bacteriostatic and anti-fungal activity. | It is used to eliminate poisons in the system. |

TABLE I-continued

| DESCRIPTION | | ACTIVE INGREDIENTS | BENEFIT |
| --- | --- | --- | --- |
| Willow Bark | White willow is a deciduous tree found in moist places in North Africa, central Asia, and in Europe, from where it was introduced into the northeastern U.S. Covered with rough, gray bark, the tree grows up to 65 feet high. In some parts of the world, it is also grow as a shrub. Its alternate, lanceolate, serrate leaves are ashy-gray in color and silky on both sides. Male and female flowers occur on separate trees and appear in catkins on leafy stalks at the same time as the leaves | Aspirin (acetylsalicylic acid). | It acts as an anti-inflammatory and as a healing agent. |
| Mullein Leaf OR Tumeric | Essential flavoring spice of Indian and other cuisine. Tumeric rhizome provides the typical yellow coloring of many curry dishes. | Curcumin (increases secretion of bile, protects liver by detoxification, stimulates gall bladder and scavenges free radicals, inhibits platelet aggregation and the enzymes which induce inflammatory prostaglandins) and essential oils (tumerone, zingiberins) | |
| Vitamin A | | Vitamin A | Helps build strong, healthy bones/joints. |
| Vitamin C | | Vitamin C | Helps build strong, healthy bones/joints. |
| Vitamin D | | Vitamin D | Helps build strong, healthy bones/joints. |
| Vitamin E | | Vitamin E | Anti-oxident. |
| Panthenol (Vitamin $B_{15}$) | | Vitamin $B_{15}$ | Anti-oxident and aids in protein synthesis, which action is improved if taken with vitamins A and E. |

If the therapeutic composition contains other constituents, then the percentages of the plantain, *aloe vera*, and other constituents are as follows: the plantain constituent is in a range of approximately 51% to 58% by weight of the therapeutic composition; the *aloe vera* constituent is in a range of approximately 37% to 39% by weight of the therapeutic composition; and the other constituents are in the range of approximately 5% to 10% by weight of the therapeutic composition.

Regardless of whether the therapeutic composition includes other constituents or not, one embodiment of the present invention has, as follows: the plantain constituent being a mixture of a glycerin-based cream or lotion and a plantain extract, in which case the glycerin-based cream or lotion is in a range of 99 to 99.9% by weight of the plantain constituent and the plantain extract is in a range of 0.1 to 1.0% by weight of the plantain constituent; and the *aloe vera* constituent being a mixture of a glycerin-based cream or lotion and *aloe vera* extract, in which case the glycerin-based cream or lotion is in a range of 90 to 99.9% by weight of the *aloe vera* constituent and the *aloe vera* extract is in a range of 0.1 to 10.0% by weight of the *aloe vera* constituent.

It should be noted that the *aloe vera* extract is derived from an *Aloe barbadensis* plant. Aloe vera or aloe may also be referred to by any of its many botanical names such as, *Aloe latifolia, Aloe peryi, Aloe saponaria,* and *Aloe tenuior.* Furthermore, *aloe vera* or aloe has numerous common names such as, Bombay aloe, Barados aloe, and Curacao aloe.

Numerous trials were performed in which the optimum percentages of the plantain, aloe vera, and herbs, if any, were discovered.

Tables II and III (below) show data from a first trial (hereinafter Trial One), wherein: in a first step, the *aloe vera* and plantain constituents are manufactured; the plantain constituent (i.e., plantain extract and glycerin-based cream or lotion) had an estimated weight of 80 grams; and the *aloe vera* constituent (i.e., *aloe vera* extract and glycerin-based cream or lotion) had an estimated weight of 60 grams.

In other words, Trial One (Tables II and III) need to be viewed as a two step process. In Step One (a), an *aloe vera* extract and constituent are processed, and in Step One (b), a plantain constituent is processed. Please note these are two independent processes. In Step Two, the *aloe vera* extract and constituent and the plantain constituent are mixed with other tinctures. The mixing process occurs using the constituents of Step One.

In the case of Trial One, Step One, there were no other constituents. Thus, with respect to Trial One, Step One, where the plantain constituent and the *aloe vera* constituent were the only two constituents of the therapeutic composition and no other constituents were added, the therapeutic composition had a total estimated weight of 140 grams so that the percentage of the plantain constituent was $80/140$ or approximately 57% and the percentage of the *aloe vera* constituent was $60/140$ or approximately 43%.

TABLE II

Trial One, Step One
Estimated Weights and Percentages of Added Active Ingredients

| | Estimated Weights | Constituent Percentage | Low Range Raw Herb | High Range Raw Herb | Low Range Total Herb | High Range Total Herb |
|---|---|---|---|---|---|---|
| Plantain Extract and Cream/Lotion | 80 grams | 80/140 = 0.5714285 | 0.1% | 1.0% | 0.0571% | 0.5714% |
| Aloe Vera Extract and Cream/Lotion | 60 grams | 60/140 = 0.4285714 | 0.1% | 10.0% | 0.0428% | 4.2857% |
| TOTAL | 140 grams | | 0.2% | 11.0% | 0.0999% | 4.8571% |

Table III (below) shows data from the second step of trial one (hereinafter Trial One, Step Two), wherein: the plantain constituent (i.e., plantain extract and glycerin-based cream or lotion) had an estimated weight of 80 grams; the *aloe vera* constituent (i.e., *aloe vera* extract and glycerin-based cream or lotion) had an estimated weight of 60 grams; and the other constituents had a combined estimated weight of 15 grams. Thus, if the therapeutic composition contained the plantain constituent, the *aloe vera* constituent, and other constituents, then the therapeutic composition had a total estimated weight of 155 grams so that the percentage of the plantain constituent was $80/155$ or approximately 51%, the percentage of the *aloe vera* constituent was $60/155$ or approximately 39%, and the percentage of other constituents was $15/155$ or approximately 10%.

Tables IV and V (below) show data from a second trial (hereinafter Trial Two), wherein: in a first step, the *aloe vera* and plantain constituents are manufactured; the plantain constituent (i.e., plantain extract and glycerin-based cream or lotion) had an estimated weight of 310 grams; and the *aloe vera* constituent (i.e., *aloe vera* extract and glycerin-based cream or lotion) had an estimated weight of 195 grams. In the case of the Trial Two, Step One, there were no other constituents. Thus, with respect to Trial Two, Step One, where the plantain constituent and the *aloe vera* constituent were the only two constituents of the therapeutic composition and no other constituents were added, the therapeutic composition had a total estimated weight of 505 grams so that the percentage of the plantain constituent was $310/505$ or approximately 51% and the percentage of the *aloe vera* constituent was $195/505$ or approximately 39%.

TABLE IV

Trial Two, Step One
Estimated Weights and Percentages of Added Active Ingredients

| | Estimated Weights | Constituent Percentage | Low Range Raw Herb | High Range Raw Herb | Low Range Total Herb | High Range Total Herb |
|---|---|---|---|---|---|---|
| Plantain Extract and Cream/Lotion | 310 grams | 310/505 = 0.6138613 | 0.1% | 1.0% | 0.0614 | 0.6138% |
| Aloe Vera Extract and Cream/Lotion | 195 grams | 195/505 = 0.3861386 | 0.1% | 10.0% | 0.0386% | 3.8613% |
| TOTAL | 505 grams | | 0.2% | 11.0% | 0.100% | 4.4751% |

Table V (below) shows data from a second step of the second trial (hereinafter Trial Two, Step Two), wherein: the

TABLE III

Trial One, Step Two
Estimated Weights and Percentages of Added Active Ingredients

| | Estimated Weights | Constituent Percentage | Low Range Raw Herb | High Range Raw Herb | Low Range Total Herb | High Range Total Herb |
|---|---|---|---|---|---|---|
| Plantain Extract and Cream/Lotion | 80 gms | 80/155 = 0.516129 | 0.1% | 1.0% | 0.0516% | 0.5161% |
| Aloe Vera Extract and Cream/Lotion | 60 gms | 60/155 = 0.3870967 | 0.1% | 10.0% | 0.3871% | 3.8710% |
| Herbal Tinctures | 15 gms | 15/155 = 0.0967741 | | | | |
| Alfalfa Leaf | 1.6667 gms | | 0.1% | 1.0% | 0.0011% | 0.0108% |
| Dandelion Root | 1.6667 gms | | 0.1% | 1.0% | 0.0011% | 0.0108% |
| Licorice Root | 1.6667 gms | | 0.1% | 1.0% | 0.0011% | 0.0108% |
| Devil's Claw | 1.6667 gms | | 0.1% | 1.0% | 0.0011% | 0.0108% |
| Feverfew | 1.6667 gms | | 0.1% | 1.0% | 0.0011% | 0.0108% |
| Chamomile | 1.6667 gms | | 0.1% | 1.0% | 0.0011% | 0.0108% |
| Yucca/Burdock | 1.6667 gms | | 0.1% | 1.0% | 0.0011% | 0.0108% |
| Willow Bark | 1.6667 gms | | 0.1% | 1.0% | 0.0011% | 0.0108% |
| Mullein Leaf | 1.6667 gms | | 0.1% | 1.0% | 0.0011% | 0.0108% |
| TOTAL | 155 grams | | 2.0% | 20.0% | 0.04484% | 4.4839% | plantain constituent (i.e., plantain extract and glycerin-based cream or lotion) had an estimated weight of 310 grams; the aloe vera constituent (i.e., aloe vera extract and glycerin-based cream or lotion) had an estimated weight of 195 grams; and the other constituents had a combined estimated weight of 25 grams. Thus, if the therapeutic composition contained the plantain constituent, the aloe vera constituent, and other constituents, then the therapeutic composition had a total estimated weight of 530 grams so that the percentage of the plantain constituent was $310/530$ or approximately 58%, the percentage of the aloe vera constituent was $195/530$ or approximately 37%, and the percentage of other constituents was $25/530$ or approximately 5%.

TABLE V

Trial Two, Step Two
Estimated Weights and Percentages of Added Active Ingredients

| | Estimated Weights | Constituent Percentage | Low Range Raw Herb | High Range Raw Herb | Low Range Total Herb | High Range Total Herb |
|---|---|---|---|---|---|---|
| Plantain Extract and Cream/Lotion | 310 gms | 310/530 = 0.5849056 | 0.1% | 1.0% | 0.0585% | 0.5849% |
| Aloe Vera Extract and Cream/Lotion | 195 gms | 195/530 = 0.3679245 | 0.1% | 10.0% | 0.0368% | 0.5849% |
| Herbal Tinctures | 25 gms | 25/530 = 0.0471698 | | | | |
| Alfalfa Leaf | 2.7778 gms | | 0.1% | 1.0% | 0.0005% | 0.0052% |
| Dandelion Root | 2.7778 gms | | 0.1% | 1.0% | 0.0005% | 0.0052% |
| Licorice Root | 2.7778 gms | | 0.1% | 1.0% | 0.0005% | 0.0052% |
| Devil's Claw | 2.7778 gms | | 0.1% | 1.0% | 0.0005% | 0.0052% |
| Feverfew | 2.7778 gms | | 0.1% | 1.0% | 0.0005% | 0.0052% |
| Chamomile | 2.7778 gms | | 0.1% | 1.0% | 0.0005% | 0.0052% |
| Yucca/Burdock | 2.7778 gms | | 0.1% | 1.0% | 0.0005% | 0.0052% |
| Willow Bark | 2.7778 gms | | 0.1% | 1.0% | 0.0005% | 0.0052% |
| Mullein Leaf | 2.7778 gms | | 0.1% | 1.0% | 0.0005% | 0.0052% |
| TOTAL | 530 grams | | 2.0% | 20.0% | 0.0999% | 4.3109% |

Table VI shows the low range averages and the high range averages between Trial One, Step One and Trial Two, Step One, wherein there were no other constituents (i.e., only plantain and aloe vera constituents).

TABLE VI

Herb Low/High Range Averages from Trial One, Step One and Trial Two, Step One

| | Constituent Percentage from Trial One, Step One to Trial Two, Step one | Low Range Average | High Range Average |
|---|---|---|---|
| Plantain Extract and Cream/Lotion | from 80/140 = 0.5714285 to 310/505 = 0.6138613 | 0.0592% | 0.5926% |
| Aloe Vera Extract and Cream/Lotion | from 60/140 = 0.4285714 to 195/505 = 0.3861386 | 0.0407% | 4.0735% |
| TOTAL | | 0.0999% | 4.6661% |

Table VII shows the low range averages and the high range averages between Trial One, Step Two and Trial Two, Step Two, wherein there were other constituents in addition to the plantain and aloe vera constituents.

TABLE VII

Herb Low/High Range Averages from Trial One, Step Two and Trial Two, Step Two

| | Constituent Percentage | Low Range Average | High Range Average |
|---|---|---|---|
| Plantain Extract and Cream/Lotion | from 80/155 = 0.516129 to 310/530 = 0.5849056 | 0.0551% | 0.5505% |
| Aloe Vera Extract and Cream/Lotion | from 60/155 = 0.3870967 to 195/530 = 0.3679245 | 0.0377% | 3.7751% |
| Herbal Tinctures | from 15/155 = 0.0967741 to 25/530 = 0.0471698 | | |
| Alfalfa Leaf | | 0.0008% | 0.0080% |
| Dandelion Root | | 0.0008% | 0.0080% |
| Licorice Root | | 0.0008% | 0.0080% |
| Devil's Claw | | 0.0008% | 0.0080% |
| Feverfew | | 0.0008% | 0.0080% |
| Chamomile | | 0.0008% | 0.0080% |
| Yucca/Burdock | | 0.0008% | 0.0080% |
| Willow Bark | | 0.0008% | 0.0080% |
| Mullein Leaf | | 0.0008% | 0.0080% |
| TOTAL | | 0.4398% | 4.3976% |

The method of preparation of aloe vera extract, plantain extract, and herbal tinctures will now be described.

For extraction of aloe vera, the leaves are cut from an aloe vera plant and sliced into thick slices. The thick slices of the aloe vera plant are then covered with glycerin and allowed to stand in a warm area. The mixture of the thick slices from the aloe vera plant covered with glycerin is then strained to yield the aloe vera extract in a solution that can be combined with a cream or lotion to be applied topically. Then, the cream or lotion, glycerin and aloe vera extract mixture can be enhanced by the addition of vitamin A, vitamin D, vitamin E, and panthenol or else any commercially available lotion containing aloe vera, vitamin A, vitamin D, vitamin E, and panthenol can be used. The vitamins, if added, have the benefit of nuturing the bones and joints and some of the vitamins may function as an anti-oxident to aid in overall health.

For extraction of plantain, the plantain leaves are harvested and thoroughly washed and rinsed. After the plantain leaves are washed and rinsed, they are ground or chopped to create a soft pulp. The pulp is placed in a container and covered with either glycerin or a high viscosity, commercially available hand cream or lotion. The container is then placed in a refrigerator or otherwise cooled for a period of time (approximately five (5) to seven (7) days). Then, the pulp and lotion mixture is put through a sieve to create a solution that contains the plantain extract or juice and leaving the pulp from the plantain leaves to be discarded. Alternatively, the extract or juice of the plantain leaves may be extracted directly by pressing the leaves. Then, extract or juice pressed from the plantain leaves is combined with a base solution, such as glycerin or a commercially available high viscosity cream or lotion.

Herbal tinctures may be purchased commercially (i.e., already prepared) or may be prepared by using either a hot or cold infusion technique, with vegetable oil, glycerin, mineral oil, or some other agent as the basic solution. The tinctures of each individual herb should be made separately and then combined with the plantain and aloe vera mixture to create the therapeutic composition.

Clinical trials on the therapeutic composition of matter of the present invention which includes a mixture of medicinal plants, such as plantain and aloe vera, with or without herbal tinctures. The clinical trials have shown that the therapeutic composition is useful in the treatment and relief of arthritic symptoms and the eradication of disease, affecting cures of clinical symptoms in acute cases, and achieving considerable improvement in chronic cases. The therapeutic composition of the present invention was applied topically on the affected site (usually, a joint) during the clinical trials until the desired results are achieved.

The therapeutic composition of matter of the present invention which includes a mixture of medicinal plants, such as plantain and aloe vera, and which does not include any herbal tinctures, has also been found useful in the treatment and relief of hematoma (particularly, to the ocular region), affecting cures of clinical symptoms in less than seven (7) days and often in as little as three or four days. The therapeutic composition of matter of the present invention should be applied topically to the affected site (i.e., area around the eye, if the hematoma is in the ocular region) until the desired results are achieved. It should be noted that for hematomas in the ocular region, the therapeutic composition of matter needs to be applied a minimum of seven times a day, whereas hematomas in other areas of the body do not need application as often.

The therapeutic composition of matter of the present invention which includes a mixture of medicinal plants, such as plantain and aloe vera, and which does not include any herbal tinctures, has also been found useful in the treatment of skin infections, affecting cures of clinical symptoms in as little as a single application. As above, the therapeutic composition should be applied topically to the affected area of skin until the desired results are achieved.

Clinical trials, which have been performed using the therapeutic composition containing at least a plantain constituent and an aloe vera constituent in a cream or lotion form applied topically and found to be helpful in the treatment and relief of the symptoms of arthritis and other afflictions, will now be described.

EXAMPLE 1

An 89-year-old female (hereinafter Subject No. 1) had an inflamed joint of the middle finger of the right hand. The joint exhibited inflammation, pain, and swelling, and was warm to the touch. In addition, the entire finger and part of the hand was affected by the pain and the swelling resulting in restricted use of the hand.

Subject No. 1 received conventional treatment of steroids. The steroids were both injected locally and ingested in the form of up to 80 mg of prednazone, which was taken orally over a period of four to five months. In both cases of the local injection and ingestion of steroids, there was some initial success in relieving both the pain and swelling, but upon elimination of the drug, the symptoms returned.

Subject No. 1 was prescribed a cream or lotion form of the therapeutic composition of the present invention and the cream or lotion was applied to the finger and hand resulting in immediate relief of the pain upon application. Approximately 2 to 3 hours after application of the cream or lotion, the pain returned, but at a somewhat diminished level. Subsequent applications of the cream or lotion with intermittent applications of dry heat resulted in relief of the symptoms in approximately three weeks and a return to normal dexterity and mobility. During this period, the frequency of the application of the cream or lotion and heat gradually diminished to three times per day without a need for augmentation of the treatment with heat.

Subject No. 1 has been treated for subsequent reoccurrences in a similar manner resulting in control of the symptoms described.

EXAMPLE 2

A 46-year-old female (hereinafter Subject No. 2) had arthritis symptoms in the wrist, knees, toes, and fingers. Onset of these symptoms can result in a two- to three-fold increase in the size of a joint, with an inflammation of the surrounding tissue. This can occur in a matter of hours and affects the associated limb resulting in substantial pain, a loss of strength in the entire limb, sleep interruption (due to pain), and general malaise due to the intensity and continuous nature of the throbbing.

In the case of Subject No. 2's toes, fingers and wrists, a cream or lotion form of the therapeutic composition of the present invention was applied topically to the affected area and augmented by the application of dry heat, such as from a heat lamp. Within two weeks, the heat applications were no longer needed and the pain and swelling had diminished greatly. Subsequent applications of the cream or lotion resulted in even further relief of the symptoms, although the results were not as dramatic. Strength was returned to the limbs.

In the case of Subject No. 2's knees, application of a cream or lotion form of the therapeutic composition of the present invention to the knee joint resulted in an increased swelling around the knee with some diminishing of the pain in the joint area. It appeared that beneath the skin, there was a poultice effect that caused the creation of a local immune response resulting in a large "pimple" under the skin. After approximately one week of treatment, the "pimple" broke sending its contents into the lower extremity of the leg. This resulted in what appeared to be a chemical imbalance causing a muscle cramp due to the increase of fluid and what is surmised to be toxins or electrolyte imbalance. Once the system eliminated this waste material, the entire limb was returned to a normal state. Strength in the limbs and joints was returned and the knee joint returned to its normal size which Subject No. 2 reported was the first time in twelve years. The knee was the only joint to exhibit this radical response and healing scenario. It is believed to be a result of the large surface area exposure that the knee offers to the topically applied treatment as compared with the relatively small surface area exposures of a toe or a finger.

In the case of Subject No. 2's wrists, one wrist had been injured due to a fall which was sustained during the course of treatment. This resulted in a rapid return of the previous symptoms, such as pain, weakness of the entire limb, and slightly increased swelling. After application of a cream or lotion form of the therapeutic composition of the present invention, these symptoms were eliminated within a fourteen-hour period. It is believed that there was a rupture or leakage of the fluid around the joint, which resulted in the symptoms and also presented the cream or lotion with the opportunity to work quickly to alleviate symptoms due to the increase surface area presented under the circumstances.

Subject No. 2 is now relatively free of pain and continues to use the cream or lotion to alleviate any remaining or subsequent symptoms that arise from time to time.

EXAMPLE 3

A 76-year-old female (hereinafter Subject No. 3) was on a blood thinner medication and had fallen in a handicap van on her way to physical therapy. The fall resulted in a black eye to the left side of the head. A cream or lotion form of the therapeutic composition of the present invention was applied four times a day to the affected area and resulted in the elimination of the symptoms in five days. After only three days, the bruise was visible only upon close examination and appeared to be yellowish orange in color.

EXAMPLE 4

A 48-year-old male (hereinafter Subject No. 4) had an infected hair follicle on the right side of his neck, which resulted in an inflamed and sensitive area of a size approximately one-half inch in diameter. Subject No. 4 had first attempted to eliminate the symptoms by applying an *aloe vera* cream or lotion and this attempt proved unsuccessful. A cream or lotion form of the therapeutic composition of the present invention was prescribed and applied to the affected area in the late afternoon. By the next morning, symptoms were eliminated and no subsequent applications were required.

EXAMPLE 5

An 83-year-old male (hereinafter Subject No. 5) complained of an insect bite of unknown origin. The area surrounding the bite was red and slightly swollen. The total diameter of the affected area was approximately two inches. The center of the affected area contained an obvious point of entry of the insect's stinger and was cherry-red in color. The remaining reddened area around the point of entry was clearly a direct result of the insect bite. Subject No. 5 had applied a cortisone-based over the counter remedy and reported no relief of the symptoms. After one application of a cream or lotion form of the therapeutic composition of the present invention, the complained-of symptoms were eliminated.

There are a number of key substances in the therapeutic composition which contribute to is effectiveness in treatment and relief of the symptoms of arthritis and other afflictions. The *aloe vera* provides a means of conducting the vitamins, herbal infusions, and tinctures through the skin to the affected area. The plantain and other herbs, which normally are taken internally, now have an opportunity to pass through the skin barrier into the affected area after topical application of the therapeutic composition of the present invention. In acute, active arthritis sites, it is the synovial membranes, and not the bone itself, that are attacked. Thus, the remedy, in most cases, has a small internal area to traverse before reaching the target site.

While it cannot repair previously deformed joints, it is believed that the curative powers of the herbs, particularly plantain, can then work on the affected joint area to alleviate the symptoms of a specified affected site. Since it is believed that the root cause of this disease is not a function of the swelling of any particular joint, it can only affect the site at which it is applied. However, the systematic elimination of the painful symptoms of each affected site will give the body the opportunity to focus its immune system response on other areas, thereby, hopefully, eliminating the root cause.

The healing process is aided by the ingestion of oral herbal medications of the same herbs used in the cream or lotion, as well as good nutrition and exercise. Exercise is very crucial in the healing process, since it has been shown that distributing the fluid surrounding the affected joint can result in a dispersion of the joint fluid resulting in a greater surface which therefore presents a greater opportunity for the cream or lotion to effectively eliminate the symptoms.

In another embodiment of the present invention, the plantain extract and *aloe vera* extract are contained in a joint compatible solution for injection directly into a joint (or a muscle near or surrounding the joint) of an applicant. The joint compatible solution may be a ringers-type solution or any other isotonic substrate. In the case of injection directly into the joint, the plantain constituent would be in the range of approximately 0.01 to 0.1% by weight of the therapeutic composition and the *aloe vera* constituent would be in the range of approximately 0.01 to 1% by weight of the therapeutic composition (i.e., more diluted, since the therapeutic composition does not have to go through the skin and muscle layers as it does with a topical application).

The therapeutic composition of the present invention may also take a form where the plantain and *aloe vera* extracts are combined with an oral hygiene agent. Then, the combination of plantain, *aloe vera*, and oral hygiene agent is included in a toothpaste base to aid in good oral hygiene.

Finally, the therapeutic composition of the present invention may have the plantain extract and *aloe vera* extract combined with a saline solution of approximately 0.05% concentration for use as a nasal spray.

The form of the invention described in the present disclosure represents only an illustrative embodiment thereof. It is to be understood that various changes may be made without departing from the teachings of the invention defined by the claimed subject matter which follows.

I claim:

1. A therapeutic composition comprising:

a plantain constituent which is in a range of approximately 0.01% to approximately 0.1% by weight of said therapeutic composition, said plantain constituent being comprised of a joint compatible solution for injection directly into a human joint and an extract from a plantain plant (*Plantago major*), said joint compatible solution being in a range of approximately 99 to approximately 99.9% by weight of said plantain constituent, and said extract from said plantain plant being in a range of approximately 0.1 to approximately 1.0% by weight of said plantain constituent, wherein said extract from said plantain plant acts as a medication to medicate tissue of an applicant below a skin barrier; and an *aloe vera* constituent, which is in a range of approximately 0.01% to approximately 1% by weight of said therapeutic composition, said *aloe vera* constituent being comprised of a joint compatible solution for injection directly into a human joint and an extract from an *aloe vera* plant (*Aloe barbadensis*), said joint compatible solution being in a range of approximately 90 to 99.9% by weight of said *aloe vera* constituent, and said extract from said *aloe vera* plant being in a range of approximately 0.1 to approximately 10.0% by weight of said *aloe vera* constituent, wherein said extract from said *aloe vera* plant acts as a vehicle to carry said extract from said plantain plant through the skin barrier of the applicant on which said therapeutic composition is injected in order to treat and relieve symptoms of any one of a group consisting of arthritis, hematomas, and infections in the tissue underlying the skin barrier.

2. A therapeutic composition comprising:

a plantain constituent which is in a range of approximately 0.01% to approximately 0.1% by weight of said therapeutic composition, said plantain constituent being comprised of a joint compatible solution for injection directly into a human joint and an extract from a plantain plant (*Plantago major*), said joint compatible solution being in a range of approximately 99 to approximately 99.9% by weight of said plantain constituent, and said extract from said plantain plant being in a range of approximately 0.1 to approximately 1.0% by weight of said plantain constituent, wherein said extract from said plantain plant acts as a medication to medicate tissue of an applicant below a skin barrier;

an *aloe vera* constituent, which is in a range of approximately 0.01% to approximately 1% by weight of said therapeutic composition, said *aloe vera* constituent being comprised of a joint compatible solution for injection directly into a human joint and an extract from an *aloe vera* plant (*Aloe barbadensis*), said joint compatible solution being in a range of approximately 90 to approximately 99.9% by weight of said *aloe vera* constituent, and said extract from said *aloe vera* plant being in a range of approximately 0.1 to approximately 10.0% by weight of said *aloe vera* constituent, wherein said extract from said *aloe vera* plant acts as a vehicle to carry said extract from said plantain plant through the skin barrier of the applicant on which said therapeutic composition is injected in order to treat and relieve symptoms of any one of a group consisting of arthritis, hematomas, and infections in the tissue underlying the skin barrier; and other herbal constituents of said therapeutic composition, wherein said other herbal constituents of said therapeutic composition is one or more of a group consisting of alfalfa leaf, dandelion root, licorice root, devil's claw, feverfew, chamomile, willow bark, any one of a group consisting of mullein leaf and tumeric, and any one of a group consisting of yucca and burdock, said other herbal constituents of said therapeutic composition being in the range of approximately 5% to approximately 10% by weight of said therapeutic composition, and wherein each of said other herbal constituents of said therapeutic composition ranges from approximately 0.1 to approximately 1.0% by weight of said other herbal constituents.

3. A method of preparing a therapeutic composition for treating any one of a group consisting of arthritis, hematomas, and infections, said method comprising the steps of:

preparing a plantain constituent, said plantain constituent being made up of a joint compatible solution for injection directly into a human joint and an extract from a plantain plant (*Plantago major*), said plantain constituent being in a range of approximately 0.01% to approximately 0.1% by weight of said therapeutic composition, wherein a weight ratio of said joint compatible solution is in a range of approximately 99 to approximately 99.9% by weight of said plantain constituent and said extract from said plantain plant is in a range of approximately 0.1 to approximately 1.0% by weight of said plantain constituent;

preparing an *aloe vera* constituent, said *aloe vera* constituent being made up of a joint compatible solution for injection directly into a human join and an extract from an *aloe vera* plant (*Aloe barbadensis*), said *aloe vera* constituent being in a range of approximately 0.01% to approximately 1% by weight of a therapeutic composition, wherein a weight ratio of said joint compatible solution is in a range of approximately 90 to approximately 99.9% by weight of said *aloe vera* constituent and said extract from said *aloe vera* plant is in a range of approximately 0.1 to approximately 10.0% by weight of said *aloe vera* constituent; and combining said plantain constituent and said *aloe vera* constituent to form said therapeutic composition for injection directly into to an applicant's joint at a site affected with any one of a group consisting of arthritis, hematomas, and infections, wherein said extract of said plantain plant acts as a medication to medicate tissue underlying a skin barrier of the applicant's skin and said extract of said *aloe vera* plant acts as a vehicle to carry said extract of said plantain plant through the skin barrier of the applicant's skin in order to treat the underlying tissue afflicted with any one of the group consisting of arthritis, hematomas, and infections.

4. The method of claim 3, wherein said preparing said plantain constituent includes the steps of:

thoroughly washing plantain leaves cut from said plantain plant;

any one of a group consisting of grinding and chopping said plantain leaves into a soft pulp;

placing said pulp in a container;

covering said pulp in said container with said joint compatible solution to create a pulp and joint compatible solution mixture;

cooling or refrigerating said pulp and joint compatible solution mixture for approximately five to seven days;

putting said pulp and joint compatible solution mixture through a sieve to create said plantain constituent containing said extract from said plantain plant; and discarding said pulp sieved from said pulp and joint compatible solution mixture.

5. The method of claim 3, wherein said preparing said *aloe vera* constituent includes the steps of:

cutting *aloe vera* leaves from said *aloe vera* plant;

slicing said *aloe vera* leaves into thick slices;

covering said thick slices of said *aloe vera* leaves with said joint compatible solution to create a mixture of the joint compatible solution and thick slices of *aloe vera* leaves;

allowing said mixture of joint compatible solution and thick slices of *aloe vera* leaves to stand in a warm area; and straining said mixture of joint compatible solution and thick slices of *aloe vera* leaves to yield said extract from said *aloe vera* plant in solution in said joint compatible solution to form said *aloe vera* constituent.

6. The method of claim 3, wherein said preparing said plantain constituent includes the steps of:

pressing leaves cut from said plantain plant to obtain said extract of said plantain plant; and combining said extract from said plantain plant with said joint compatible solution.

7. The method of claim 3, wherein said preparing said *aloe vera* constituent includes the steps of:

cutting *aloe vera* leaves from said *aloe vera* plant;

slicing said *aloe vera* leaves into thick slices;

covering said thick slices of said *aloe vera* leaves with joint compatible solution to create a mixture of joint compatible solution and thick slices of *aloe vera* leaves;

allowing said mixture of joint compatible solution and thick slices of *aloe vera* leaves to stand in a warm area; and straining said mixture of joint compatible solution and thick slices of *aloe vera* leaves to yield said extract from said *aloe vera* plant in solution for combination with a joint compatible solution.

8. The method of claim 3, wherein said preparing said plantain constituent includes the steps of:

thoroughly washing plantain leaves cut from said plantain plant;

grinding or chopping said plantain leaves into a soft pulp;

placing said pulp in a container;

covering said pulp in said container with said joint compatible solution to create a pulp and joint compatible solution mixture;

cooling or refrigerating said pulp and joint compatible solution mixture for approximately five to seven days;

putting said pulp and joint compatible solution mixture through a sieve to create said plantain constituent containing said extract from said plantain plant; and discarding said pulp sieved from said pulp and joint compatible solution mixture.

9. The method of claim 3, wherein said combining of said plantain constituent and said *aloe vera* constituent includes combining a tincture of one or more of the group consisting of alfalfa, dandelion root, licorice root, devil's claw, fererfew, chamomile, willow bark, mullein leaf, tumeric, yucca and burdock to form said therapeutic composition.

10. A therapeutic composition produced by a process comprising the steps of:

preparing a plantain constituent of said therapeutic composition, wherein said plantain constituent of said therapeutic composition is made up of an extract from a plantain plant combined with a joint compatible solution such that a weight ratio of said joint compatible solution is in a range of approximately 90 to approximately 99.9% by weight of said plantain constituent of said therapeutic composition and said extract from said plantain plant is in a range of approximately 0.1 to approximately 10.0% by weight of said plantain constituent of said therapeutic composition, said plantain constituent of said therapeutic composition being in a range of approximately 0.01% to approximately 0.1% by weight of said therapeutic composition;

preparing an *aloe vera* constituent of said therapeutic composition, wherein said *aloe vera* constituent of said therapeutic composition is made up of an extract from an *aloe vera* plant combined with a joint compatible solution such that a weight ratio of said joint compatible solution is in a range of approximately 90 to approximately 99.9% by weight of said *aloe vera* constituent of said therapeutic composition and said extract from said *aloe vera* plant is in a range of approximately 0.1 to approximately 10.0% by weight of said *aloe vera* constituent of said therapeutic composition, said *aloe vera* constituent of said therapeutic composition being in a range of approximately 0.01% to approximately 1% by weight of a therapeutic composition; and combining said plantain constituent and said *aloe vera* constituent to form said therapeutic composition for injection directly into a human joint of an applicant at a site affected with any one of a group consisting of arthritis, hematomas, skin rashes, and infections.

11. The therapeutic composition produced by the process of claim 10, wherein the step of preparing said plantain constituent of said therapeutic composition includes the steps of:

washing plantain leaves cut from said plantain plant thoroughly;

grinding or chopping said plantain leaves into a soft pulp;

placing said soft pulp into a container;

covering said soft pulp in said container with a joint compatible solution to create a pulp and joint compatible solution mixture;

cooling or refrigerating said pulp and joint compatible solution mixture for approximately five to seven days;

putting said pulp and joint compatible solution mixture through a sieve to create said plantain constituent of said therapeutic composition containing said extract from said plantain plant; and discarding said pulp sieved from said pulp and joint compatible solution mixture.

12. The therapeutic composition produced by the process of claim 10, wherein the step of preparing said *aloe vera* constituent of said therapeutic composition includes the steps of:

cutting said *aloe vera* leaves from said *aloe vera* plant;

slicing said *aloe vera* leaves into thick slices;

covering said thick slices of said *aloe vera* leaves with a joint compatible solution to create a mixture of joint compatible solution and thick slices of *aloe vera* leaves;

allowing said mixture of joint compatible solution and thick slices of *aloe vera* leaves to stand in a warm area; and straining said mixture of joint compatible solution and thick slices of *aloe vera* leaves to yield extract of said *aloe vera* plant in solution in said *aloe vera* constituent of said therapeutic composition.

13. The therapeutic composition produced by the process of claim 10, wherein the step of preparing said plantain constituent of said therapeutic composition includes the steps of:

pressing leaves cut from said plantain plant to obtain said extract from said plantain plant; and combining said extract from said plantain plant with a joint compatible solution.

14. The therapeutic composition produced by the process of claim 10, wherein the step of preparing said *aloe vera* constituent of said therapeutic composition includes the steps of:

cutting *aloe vera* leaves from said *aloe vera* plant;

slicing said *aloe vera* leaves into thick slices;

covering said thick slices of said *aloe vera* leaves with joint compatible solution to create a mixture of joint compatible solution and thick slices of *aloe vera* leaves;

allowing said mixture of joint compatible solution and thick slices of *aloe vera* leaves to stand in a warm area; and straining said mixture of joint compatible solution and thick slices of *aloe vera* leaves to yield said extract from said *aloe vera* plant in solution in said joint compatible solution to form said *aloe vera* constituent of said therapeutic composition.

15. The therapeutic composition produced by the process of claim 10, wherein the step of preparing said plantain constituent of said therapeutic composition includes the steps of:

washing plantain leaves cut from said plantain plant thoroughly;

grinding or chopping said plantain leaves into a soft pulp;

placing said soft pulp into a container;

covering said soft pulp in said container with a joint compatible solution to create a pulp and joint compatible solution mixture;

cooling or refrigerating said pulp and joint compatible solution mixture for approximately five to seven days;

putting said pulp and joint compatible solution mixture through a sieve to create said plantain constituent of said therapeutic composition containing said extract of said plantain plant; and discarding a remnant sieved from said pulp and joint compatible solution mixture.

16. The therapeutic composition produced by the process of claim 11, wherein the step of preparing said *aloe vera* constituent of said therapeutic composition includes the steps of:

cutting said *aloe vera* leaves from said *aloe vera* plant;

slicing said *aloe vera* leaves into thick slices;

covering said thick slices of said *aloe vera* leaves with a joint compatible solution to create a mixture of joint compatible solution and thick slices of *aloe vera* leaves;

allowing said mixture of joint compatible solution and thick slices of *aloe vera* leaves to stand in a warm area; and straining said mixture of joint compatible solution and thick slices of *aloe vera* leaves to yield said extract of said *aloe vera* plant in solution in said joint compatible solution to form said *aloe vera* constituent of said therapeutic composition.

17. The therapeutic composition produced by the process of claim 16, wherein the step of preparing said plantain constituent of said therapeutic composition and the step of preparing said *aloe vera* constituent of said therapeutic composition includes combining a tincture of one or more of the group consisting of alfalfa leaf, dandelion root, licorice root, devil's claw, feverfew, chamomile, willow bark, mullein leaf, tumeric, yucca, and burdock to form said therapeutic composition.

* * * * *